(12) United States Patent
Biesinger et al.

(10) Patent No.: US 11,464,461 B1
(45) Date of Patent: Oct. 11, 2022

(54) ANNOTATIONS OF CONTINUOUS GLUCOSE MONITORING DATA

(71) Applicant: Verily Life Sciences LLC, Mountain View, CA (US)

(72) Inventors: William Jacob Benhardt Biesinger, Fremont, CA (US); Joshua Burkart, Boston, MA (US)

(73) Assignee: Verily Life Sciences LLC, Mountain View, CA (US)

( * ) Notice: Subject to any disclaimer, the term of this patent is extended or adjusted under 35 U.S.C. 154(b) by 293 days.

(21) Appl. No.: 16/816,151

(22) Filed: Mar. 11, 2020

Related U.S. Application Data

(63) Continuation of application No. 15/891,291, filed on Feb. 7, 2018, now Pat. No. 10,624,591.

(51) Int. Cl.
| | | |
|---|---|---|
| *A61B 5/00* | (2006.01) | |
| *G16H 40/63* | (2018.01) | |
| *G16H 10/60* | (2018.01) | |
| *A61B 5/145* | (2006.01) | |

(52) U.S. Cl.
CPC .......... *A61B 5/746* (2013.01); *A61B 5/14532* (2013.01); *A61B 5/7267* (2013.01); *A61B 5/742* (2013.01); *G16H 10/60* (2018.01); *G16H 40/63* (2018.01)

(58) Field of Classification Search
CPC ... A61B 5/746; A61B 5/14532; A61B 5/7267; A61B 5/742; G16H 10/60; G16H 40/63
USPC ........................................................ 705/2–3
See application file for complete search history.

(56) References Cited

U.S. PATENT DOCUMENTS

| | | | |
|---|---|---|---|
| 6,553,386 B1 | 4/2003 | Alabaster | |
| 8,249,946 B2 | 8/2012 | Froseth et al. | |
| 8,597,570 B2 | 12/2013 | Terashima et al. | |
| 2002/0032583 A1 | 3/2002 | Joao | |
| 2008/0201169 A1 | 8/2008 | Galasso et al. | |
| 2008/0208027 A1* | 8/2008 | Heaton .................. | G16H 40/67 600/365 |
| 2013/0325504 A1 | 12/2013 | Greene et al. | |

(Continued)

OTHER PUBLICATIONS

Albers, David J., et al., "Personalized glucose forecasting for type 2 diabetes using data assimilation", "Personalized glucose forecasting for type 2 diabetes using data assimilation;" PLoS Comput Biol 13(4): e1005232. https://doi.org/10.1371/journal.pcbi.1005232; Apr. 27, 2017;, Apr. 27, 2017, 1-38.

(Continued)

*Primary Examiner* — Michael Tomaszewski
(74) *Attorney, Agent, or Firm* — Perkins Coie LLP

(57) ABSTRACT

Introduced here are diabetes management platforms able to make annotations to physiological data of a subject whose glycemic health state is being monitored. These annotations can be used to classify excursions detected in the physiological data to facilitate the identification of a therapeutic behavior change intended to improve the glycemic health state of the subject. For example, a health coach may review the annotation(s) associated with the subject before generating a recommendation for improving the glycemic health state. As another example, the diabetes management platform can automatically identify an appropriate recommendation based on the annotation(s).

20 Claims, 10 Drawing Sheets

(56) References Cited

U.S. PATENT DOCUMENTS

| | | | |
|---|---|---|---|
| 2015/0045641 A1* | 2/2015 | Rule | A61B 5/150229 |
| | | | 600/347 |
| 2015/0141770 A1 | 5/2015 | Rastogi et al. | |
| 2015/0289823 A1* | 10/2015 | Rack-Gomer | A61B 5/168 |
| | | | 600/365 |
| 2016/0378937 A1 | 12/2016 | Soni et al. | |
| 2017/0128007 A1 | 5/2017 | Hayter et al. | |
| 2017/0185748 A1* | 6/2017 | Budiman | G16H 50/20 |
| 2017/0220751 A1 | 8/2017 | Davis et al. | |
| 2018/0197628 A1 | 7/2018 | Wei et al. | |
| 2019/0290172 A1 | 9/2019 | Hadad et al. | |

OTHER PUBLICATIONS

Lim, Teck-Onn, et al., "Bimodality in Blood Glucose Distribution", "Bimodality in Blood Glucose Distribution; Is it universal?"; Clinical Research Centre, the Department of Nephrology, and the Public Health Institute, Kuala Lumpur, Malaysia; Apr. 10, 2002; pp. 2212-2217;, Apr. 10, 2002, 2212-2217.

Wittinghoff, Eric , et al., "Regression Methods in Biostatistics", Regression Methods in Biostatistics: Linear, Logistic, Survival, and Repeated Measures Models; ISBN 0-387-20275-7; San Francisco, CA; Oct. 2004;, Oct. 2004, 346 pages.

\* cited by examiner

600

601

Acquire physiological data generated by a glucose monitoring device

602

Post a visualization of the physiological data as a glucose trace over time to an interface for review by an individual

603

Examine the physiological data to detect an excursion in the blood glucose level

604

Classify the excursion as being indicative of a glycemic event

605

Identify an annotation corresponding to the glycemic event

606

Cause display of the annotation on the interface accessible to the individual

607

Store an indication of the annotation in a database to create a historical record of annotations associated with a subject

Generate an interface accessible to an individual

702

Post a visualization of a physiological data series as a glucose trace to the interface for review by the individual

703

Generate a visualization component by populating separate track(s) with annotation(s)

704

Dynamically modify the visualization and/or the visualization component in real time

705

Estimate the glycemic health state of the subject based on the visualization and/or visualization component

706

Estimate a glucose-related metric based on the physiological data series

707

Receive input indicative of feedback provided through the interface

708

Cause display of a notification by another computer program executing on another computing device

FIGURE 7

ANNOTATIONS OF CONTINUOUS GLUCOSE MONITORING DATA

CROSS-REFERENCE TO RELATED APPLICATIONS

This application is a continuation of U.S application Ser. No. 15/891,291, filed Feb. 7, 2018, which is incorporated by reference herein in its entirety.

TECHNICAL FIELD

Various embodiments concern computer programs and associated computer-implemented techniques for characterizing time intervals of continuous glucose monitor readings with annotations.

BACKGROUND

After ingestion of a foodstuff that contains carbohydrates, the human body breaks down the carbohydrates into glucose, which serves as a source of energy for the cells of the human body. Glucose is transported via circulation within the blood stream. Therefore, ingestion of foodstuffs will influence the concentration of glucose within the blood stream (also referred to as the "blood glucose level" or "glucose level").

According to the American Diabetes Association (ADA), a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 6 depicts a flow diagram of a process for making annotations to physiological data specifying the blood glucose level of a subject whose glycemic health state is being monitored.

FIG. 7 depicts a flow diagram of a process for facilitating the acquisition of feedback from an individual for improving the glycemic health state of a subject whose blood glucose level is being monitored.

Figure 1:
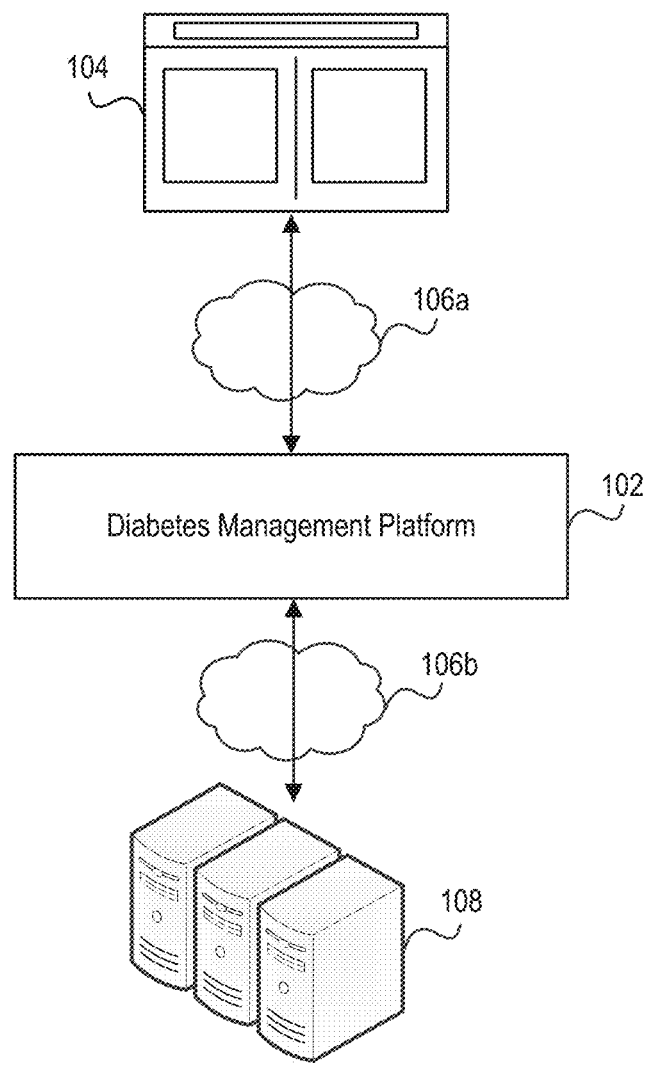
FIG. 1 illustrates a network environment that includes a diabetes management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Diabetes mellitus (commonly referred to as "diabetes") is a group of metabolic disorders in which the affected individuals experience high blood glucose levels over a prolonged period. If left untreated, diabetes can cause many complications. For example, long-term complications can include cardiovascular disease, stroke, chronic kidney disease, foot ulcers, and eye damage.

Individuals with diabetes can benefit from education about treatment, good nutrition to achieve a normal body weight, and exercise. However, some of those individuals may find it difficult to implement lifestyle changes that promote healthier blood glucose levels. Moreover, some of these individuals may find it difficult to understand blood glucose level measurements, which represent a technical signal indicative of the diabetes disease state.

Blood glucose monitoring is the process through which the concentration of glucose within the blood stream (also referred to as the "blood glucose level" or "glucose level") is tested. A test is typically performed by piercing the skin to draw blood, and then applying the blood to a disposable, chemically active test strip. Historically, an individual with diabetes would take several measurements throughout the day in an ad hoc manner using a blood glucose meter. Because blood glucose meters require that individuals manually perform each test, measurements are often generated sporadically, which can make it difficult to accurately estimate the glycemic health state of an individual.

Continuous glucose monitoring represents a promising new way for individuals to gain insights into the diabetes disease state. In contrast to a blood glucose meter, a continuous glucose monitor can continually monitor the blood glucose level throughout the day. For example, a continuous glucose monitor may automatically take blood glucose measurements every five minutes, ten minutes, etc. Thus, an individual may be able to observe how consumption of a certain foodstuff or performance of a certain activity affects blood glucose level.

Visualizations can be helpful in conveying the importance of blood glucose level variations detected in the physiological data generated by these glucose monitoring devices. For example, physiological data generated by a glucose monitoring device may be represented as a glucose trace over time. While glucose traces allow variations to be readily observed in a visual manner, these glucose traces can be difficult to qualitatively interpret, even for professional diabetes educators and health coaches responsible for monitoring the glycemic health of individuals with diabetes (also referred to as "subjects" or "patients").

Introduced here, therefore, are computer programs and associated computer-implemented techniques for making annotations to physiological data of a subject whose glycemic health state is being monitored. These annotations can be used to classify excursions detected in the physiological data to facilitate the identification of a therapeutic behavior change intended to improve the glycemic health state of the subject. For example, a health coach may review the annotation(s) associated with the subject before generating a recommendation for improving the glycemic health state.

An annotation can convey information about causes (e.g., meal intake events) and/or effects (e.g., glycemic events of a certain type, intensity, etc.) related to the glycemic health state. For example, in some embodiments annotations visually indicate the causes of glycemic events (e.g., by distinguishing different types of causes based on color), while in other embodiments annotations visually indicate the effects of glycemic events (e.g., by distinguishing different types of effects based on color). Accordingly, annotations can assist a subject in better understanding the causes and effects of their behaviors with respect to the glycemic health state.

A diabetes management platform can initially acquire physiological data generated by glucose monitoring device. Generally, the glucose monitoring device is a continuous glucose monitor that continually monitors the blood glucose level of a subject. The physiological data, therefore, may include discrete, digitally represented data values indicative of the blood glucose concentration as sampled periodically. In such embodiments, each data value may be one of a series of data values in a temporal order. However, the glucose monitoring device could also be a blood glucose monitor that monitors the blood glucose level of the subject on an ad hoc basis. Thus, the physiological data could include discrete, digitally represented data values indicative of the blood glucose concentration as sampled ad hoc.

The diabetes management platform can then examine the physiological data to detect an excursion in the blood glucose level of the subject. More specifically, the diabetes management platform can detect a signal feature defined by one or more data values. Examples of signal features include the minimum blood glucose value, the maximum blood glucose value (also referred to as the "peak blood glucose value"), the total area beneath the peak blood glucose value (i.e., an integral of a glucose trace over the duration of the peak blood glucose value), a recovery rate following the peak blood glucose value, a time characteristic of the minimum or peak blood glucose values, etc.

The diabetes management platform can classify the excursion as being indicative of a glycemic event. Moreover, the diabetes management platform may identify an appropriate annotation based on the glycemic event. Said another way, the diabetes management platform may identify the annotation based on the signal feature detected in the physiological data. In some embodiments, the diabetes management platform causes display of the physiological data as a glucose trace over time to an interface generated by a computer program. In such embodiments, the diabetes management platform can cause display of the annotation on the interface. The glucose trace and the annotation can be aligned with respect to a common time axis, thereby visually alerting a viewer of potential changes in the glycemic condition (also referred to as the "glycemic health state") of the subject.

Such action requires that the diabetes management platform go beyond detecting excursions. For example, the diabetes management platform will often apply rule set(s) to characterize continuous windows of physiological data with different annotation(s). Moreover, the diabetes management platform may annotate a window of physiological data with an actionable, comparable glycemic health assessment indicative of a characteristic of the biological system of the subject. Visual presentation of these annotations in line with a glucose trace can facilitate the discovery of the glycemic health state, the recommendation of a therapeutic behavior change for improving the glycemic health state, the identification of comparable subjects and/or glycemic events, etc.

Embodiments may be described with reference to particular computer programs, system configurations, networks, etc. However, those skilled in the art will recognize that these features are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program an electronic device to perform a process for examining physiological data generated by a glucose monitoring device, discovering excursions in the physiological data, identifying real-world events and/or circumstances corresponding to the excursions, producing visualizations of the physiological data that include annotation(s), etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on." Moreover, the terms "based on at least" and "at least based on" includes, in some cases or embodiments, based only on. Said another way, a measure calculated based on at least a certain feature may be based only on that feature.

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 illustrates a network environment 100 that includes a diabetes management platform 102. Individuals can interface with the diabetes management platform 102 via an interface 104. The diabetes management platform 102 may be responsible for parsing physiological data pertaining to an individual to discover excursions in the blood glucose level, classify the excursions as glycemic events, generate recommendations for guiding the individual toward a healthier glycemic health state, etc. The diabetes management platform 102 may also be responsible for creating interfaces through which the individual can view physiological data, manage preferences, etc.

Physiological data could specify the blood glucose level of the individual accessing the interface 104 or some other person. For example, in some embodiments the interface 104 enables a person with diabetes to view their own physiological data, while in other embodiments the interface 104 enables an individual to view physiological data associated with some other person. The individual may be a health coach responsible for monitoring the glycemic health of the other person. Examples of health coaches include medical professionals (e.g., a physician or nurse), diabetic health counselors, family members of the other person, etc. Some interfaces are configured to facilitate interactions between subjects and health coaches, while other interfaces are configured to serve as informative dashboards for subjects.

As noted above, the diabetes management platform 102 may reside in a network environment 100. Thus, the diabetes management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. Additionally or alternatively, the diabetes management platform 102 can be communicatively coupled to computing device(s) over a short-range communication protocol, such as Bluetooth® or Near Field Communication (NFC).

The interface 104 is preferably accessible via a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diabetes management platform 102 are hosted locally. That is, the diabetes management platform 102 may reside on the computing device used to access the interface 104. For example, the diabetes management platform 102 may be embodied as a mobile application executing on a mobile phone. Other embodiments of the diabetes management platform 102 are executed by a cloud computing service operated by Amazon Web Services® (AWS), Google Cloud Platform™, Microsoft Azure®, or a similar technology. In such embodiments, the diabetes management platform 102 may reside on a host computer server that is communicatively coupled to one or more content computer servers 108. The content computer server(s) 108 can include different types of data, user information (e.g., profiles, credentials, and health-related information such as age, diabetes classification, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., physiological data, healthcare regimen data, and processing operations) to be downloaded at a single point in time or on a periodic basis (e.g., weekly, daily, or hourly).

Figure 2:
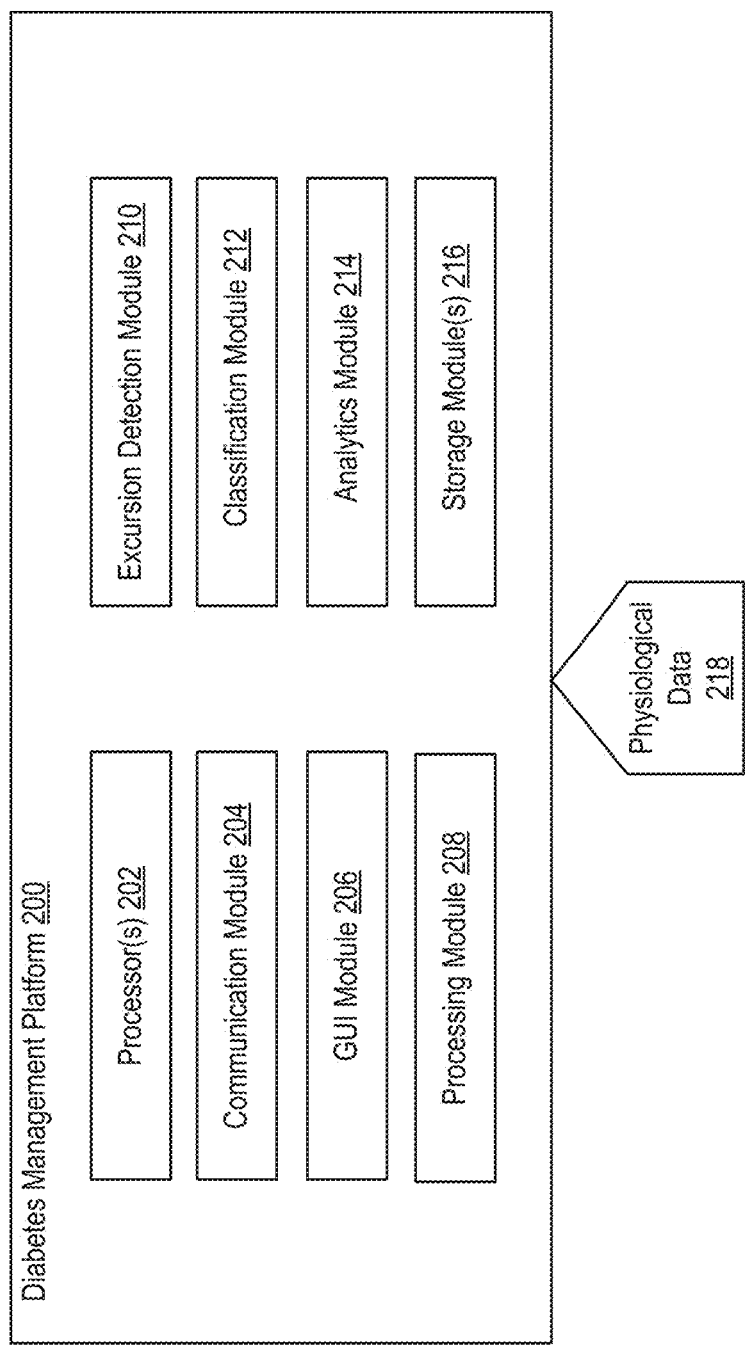
FIG. 2 depicts the high-level architecture of a diabetes management platform able to analyze physiological data to detect excursions in the blood glucose level of a subject.

FIG. 2 depicts the high-level architecture of a diabetes management platform 200 able to analyze physiological data 218 to detect excursions in the blood glucose level of a subject. The diabetes management platform 200 may use these excursions to compile annotations for review by an individual. As shown in FIG. 1, the individual can interface with the diabetes management platform 200 via an interface. The individual may be a person with diabetes or another person with an interest in the blood glucose level of the person with diabetes.

The diabetes management platform 200 can include one or more processors 202, a communication module 204, a graphical user interface (GUI) module 206, a processing module 208, an excursion detection module 210, a classification module 212, an analytics module 214, and one or more storage modules 216. In some embodiments a single storage module includes multiple computer programs for performing different operations (e.g., format conversion and statistical analysis), while in other embodiments each computer program is hosted within a separate storage module. Embodiments of the diabetes management platform 200 may include some or all of these components, as well as other components not shown here.

The processor(s) 202 can execute modules from instructions stored in the storage module(s) 216, which can be any device or mechanism capable of storing information. For example, the processor(s) 202 may execute the GUI module 206, processing module 208, excursion detection module 210, classification module 212, and analytics module 214.

The communication module 204 can manage communications between various components of the diabetes management platform 200. The communication module 204 can also manage communications between the computing device on which the diabetes management platform 200 resides and another computing device.

For example, the diabetes management platform 200 may reside on a mobile phone in the form of a mobile application. In such embodiments, the communication module 204 can facilitate communication with a network-accessible computer server responsible for supporting the mobile application. The communication module 204 may facilitate communication with various data sources through the use of application programming interfaces (APIs), bulk data interfaces, etc.

As another example, the diabetes management platform 200 may reside on a server system that includes one or more network-accessible computer servers. In such embodiments, the communication module 204 can communicate with a computer program executing on the computing device associated with the individual. Those skilled in the art will recognize that the components of the diabetes management platform 200 can be distributed between the server system and the computing device associated with the individual in various manners. For example, some data (e.g., physiological data) may reside on the computing device of the individual, while other data (e.g., processing operations for detecting excursions in the physiological data 218 and rule sets for identifying appropriate annotations, recommendations, etc.) may reside on the server system.

The GUI module 206 can generate the interface(s) through which an individual can interact with the diabetes management platform 200. For example, an interface may include a graphical representation of the blood glucose level over time and one or more annotations that characterize corresponding window(s) of physiological data 218. As another example, an interface may specify a characteristic of the physiological data 218 or a specific data value. These interfaces may also present feedback/suggestions for improving the glycemic health state (e.g., by performing certain activities, refraining from consuming certain foodstuffs, etc.).

The processing module 208 can apply one or more operations to the physiological data 218 acquired by the diabetes management platform 200. Physiological data 218 specifying the blood glucose level of an individual could be generated by a glucose monitoring device. Examples of glucose monitoring devices include continuous glucose monitors and blood glucose meters.

A glucose monitoring device may be configured to continuously or periodically transmit physiological data 218 to the diabetes management platform 200. In some embodiments, the glucose monitoring device continually uploads physiological data 218 to the diabetes management platform 200 so long as the glucose monitoring device remains communicatively coupled to the computing device on which the diabetes management platform 200 resides (e.g., via a Bluetooth® communication channel). In other embodiments, the glucose monitoring device uploads physiological data 218 to the diabetes management platform 200 on a periodic basis (e.g., hourly, daily, or weekly). In such embodiments, the physiological data 218 may include multiple data sets (e.g., a first data set for a first time interval, a second data set for a second time interval, etc.). Each time interval could be associated with, and correspond to, a natural rhythm or cycle. Examples of natural rhythms/cycles include a circadian cycle, a menstrual cycle, a feeding cycle, an elimination cycle, etc.

The processing module 208 can process the physiological data 218 into a format suitable for the other modules (e.g., the excursion detection module 210, classification module 212, analytics module 214, or storage module(s) 216). The processing module 208 can also parse the physiological data 218 to identify certain characteristic(s) of the blood glucose level. For example, the processing module 208 may calculate metrics that are critical in guiding diabetes treatment in a personalized manner. These metrics can include time-in-range, glycemic variability, glycemic exposure, hypoglycemia range, hyperglycemia range, etc.

The excursion detection module 210 can examine the physiological data 218 to detect excursions in the blood glucose level. Each excursion is defined by one or more data values specifying the blood glucose level at corresponding time(s). More specifically, the excursion detection model 210 can parse the physiological data 218 to detect a signal feature that should be flagged for further analysis. Examples of signal features include:

a minimum blood glucose value;

a maximum blood glucose value (also referred to as a "peak blood glucose value");

a total area beneath the peak blood glucose value (i.e., an integral of a glucose trace over the duration of the peak blood glucose value);

an area beneath the glucose trace during the duration that is outside the glycemic range recommended by the American Diabetes Association (ADA);

a recovery rate following the peak blood glucose value;

a recovery rate following the minimum blood glucose value (e.g., due to consumption of a foodstuff); and a time characteristic of the peak blood glucose value or the minimum blood glucose value.

The recovery rates may be used to determine how symmetric the minimum or peak blood glucose values are. The time characteristic, meanwhile, could be the actual time (e.g., 8:00 AM, 10:30 AM, etc.), the day of the week, or an indication of the time interval. For example, the excursion detection model 210 may simply specify whether a glycemic event occurred during the morning interval, afternoon interval, evening interval, or night interval.

Thus, while some excursions may be defined by blood glucose level variations exceeding a specified amount, other excursions may be based on the magnitude of a single data value (e.g., in the case of the minimum and peak blood glucose values). Similarly, the excursion detection module 210 may identify excursions by applying processing algorithm(s) to identify data value(s) that match a pattern in accordance with a pattern-defining parameter. Additionally or alternatively, the excursion detection module 210 could train a classification model to identify the data value(s) responsive to a determination that a matching window of physiological data corresponds to a foodstuff consumption event (also referred to as a "meal"). A "matching window" is a segment of physiological data 218 that temporally matches the glycemic event. The classification model can be trained using a supervised machine learning algorithm.

The classification model 212 can classify each excursion as being indicative of a glycemic event. Because each glycemic event is digitally represented by the data value(s) defining the excursion, a glycemic event can be thought of as a logical categorization of the signal feature and/or the data value(s). The classification model 212 can also identify/compile an annotation based on the glycemic event. More specifically, the classification model 212 can make annotations to the physiological data 218 to visually identify instances of glycemic events. Generally, each annotation is posted to an interface generated by the GUI module 206 as a visualization component. For example, the GUI module 206 may generate a graph that includes the physiological data 218 as a glucose trace over time and one or more annotations. The glucose trace and the annotation(s) may be aligned with respect to a common time axis, thereby visually alerting a viewer of potential changes in the glycemic health state of the subject.

The analytics module 214 can perform one or more analytic processes using the physiological data 218. In some embodiments, the analytics module 214 performs an analytic process using a specific window of the physiological data 218 corresponding to a glycemic event, a certain time interval (e.g., morning, afternoon, evening, or night), etc. Such action may be performed selectively. For instance, the analytics module 214 may only perform the analytic process (es) responsive to discovering the data values are indicative of bad glycemic health, good glycemic health, a downward trend in glycemic health, an upward trend in glycemic health, etc. Examples of analytic processes include prioritizing recommendations provided for improving the glycemic health state of the subject, examining glucose-related metrics critical in guiding diabetes treatment in a personalized manner, filtering certain data values from the physiological data 218 that are not to be examined by the excursion detection module 210, etc.

As noted above, continuous glucose monitoring represents a promising new way for individuals to gain insights into the diabetes disease state. The blood glucose level will increase following the ingestion of a foodstuff, and then steadily decrease thereafter. Foodstuffs having a high glycemic index are more rapidly digested, and thus cause substantial fluctuations in the blood glucose level over a short period of time.

According to the ADA, a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range. For example, individuals with blood glucose levels that are consistently above 7.0 mmol/L (126 mg/dL) are generally considered to have hyperglycemia, while individuals with blood glucose levels that are consistently below 4.0 mmol/L (70 mg/dL) are generally considered to have hypoglycemia.

Figure 3:
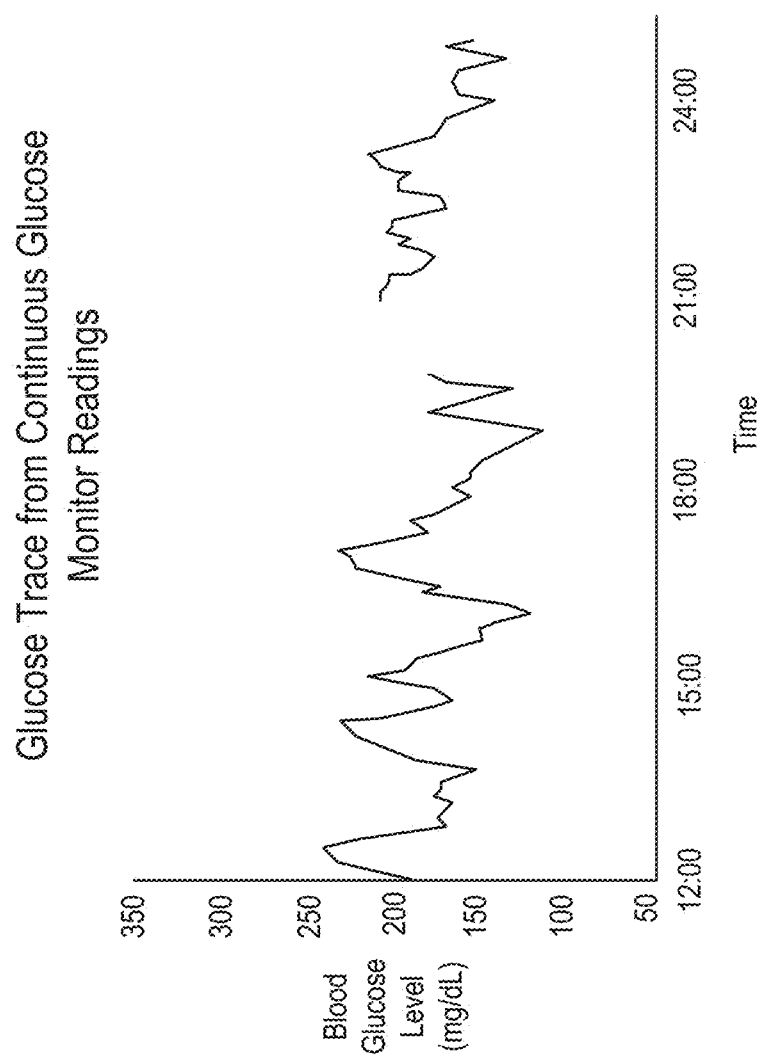
FIG. 3 depicts an example of a glucose trace constructed from a series of measurements generated by a continuous glucose monitor over the course of a 12-hour period.

Visualizations can be helpful in conveying the importance of blood glucose level variations detected by these glucose monitoring devices. One example is a glucose trace constructed from a series of measurements generated by a continuous glucose monitor over the course of a 12-hour period, as shown in FIG. 3. Glucose traces enable individuals to readily observe how consumption of a certain foodstuff or performance of a certain activity affects blood glucose level. However, glucose traces can be difficult to qualitatively interpret, even for professional diabetes educators and health coaches responsible for monitoring the glycemic health of individuals with diabetes (also referred to as "subjects" or "patients").

Introduced here, therefore, are computer programs and associated computer-implemented techniques for making annotations to physiological data of a subject whose glycemic health state is being monitored. More specifically, a diabetes management platform can apply rule set(s) to the physiological data to discover glycemic events, propose therapeutic behavior changes, etc. Thus, the diabetes management platform can automatically surface reminders regarding certain actions, interesting glycemic characteristics (e.g., the blood glucose level was abnormally low upon waking or abnormally high during the evening), etc. The diabetes management platform can provide these insights instead of, or in addition to, those offered by health coaches.

These annotations can be used to classify excursions detected in the physiological data to facilitate the identification of a therapeutic behavior change intended to improve the glycemic health state of the subject. For example, a health coach may review the annotation(s) associated with a subject before generating a recommendation for improving the glycemic health state. As another example, the diabetes management platform may automatically generate a recommendation for improving the glycemic health state based on the annotations and/or other characteristics of the excursion(s), such as duration, frequency, intensity, etc.

Figure 4:
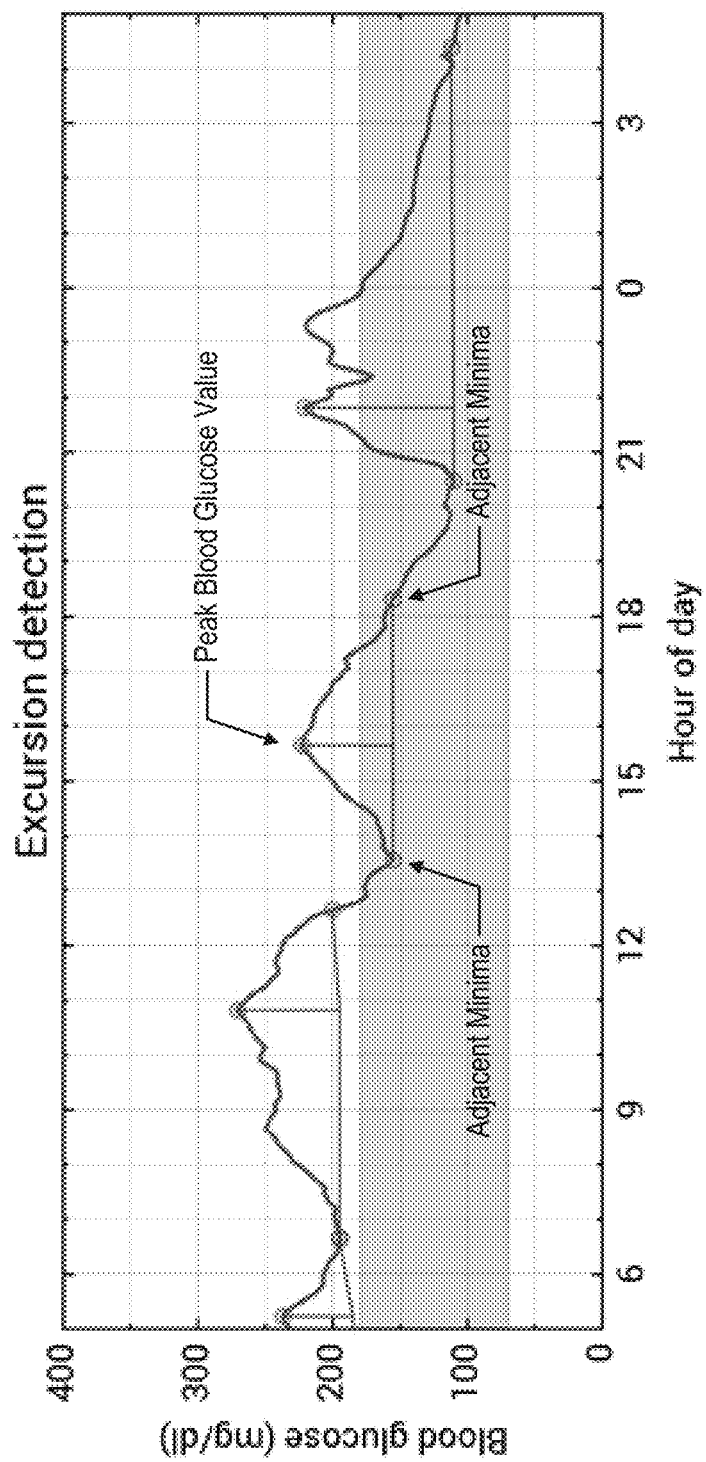
FIG. 4 illustrates how the diabetes management platform can apply processing algorithm(s) to detect excursions in the blood glucose level that are caused by meals.

FIG. 4 illustrates how the diabetes management platform can apply processing algorithm(s) to detect excursions in the blood glucose level that are caused by meals. An excursion is a variation in the blood glucose level exceeding a specified amount within a predetermined time interval. Generally, the variation will be a positive variation (e.g., due to consumption of a foodstuff), though the variation could also be a negative variation. In some embodiments excursions are detected based only on a time series of blood glucose level values, while in other embodiments excursions are detected based on other information in addition to the time series of blood glucose level values. The other information may include metadata, user input, other signals (e.g., from a glucose monitoring device, fitness tracker, mobile phone, etc.), etc. The diabetes management platform may also apply other processing algorithm(s) to detect excursions caused by other types of glycemic events. For example, some embodiments of the diabetes management platform examine the glycemic recovery following meals due to, for example, performance of an exercise activity.

By applying the processing algorithm(s), the diabetes management platform can detect semi-global minima over a configurable time interval. Thus, the diabetes management platform may find the time interval boundaries that permit the blood glucose level to be a global minimum within a surrounding time interval. In some embodiments the time intervals are manually defined by an individual, while in other embodiments the time intervals are automatically defined by the diabetes management platform. For example, the diabetes management platform may set the time intervals to match a natural rhythm/cycle, such as a circadian cycle, menstrual cycle, feeding cycle, elimination cycle, etc.

The diabetes management platform can then pair adjacent minima and ensure that a sufficiently large excursion occurs in between the adjacent minima. An excursion may be sufficiently large if the peak blood glucose value exceeds an upper threshold, if the difference between the peak blood glucose value and the adjacent minima exceeds a certain amount, etc. Additionally or alternatively, the excursion may be defined based on the relationship between the adjacent minima and/or the peak blood glucose value and the glycemic range recommended by the ADA. Thus, the processing algorithm(s) can include two parameters (i.e., the semi-global minima and the peak blood glucose value) that are fit to physiological data generated by a glucose monitoring device.

Several different heuristics and/or algorithms can be implemented by the diabetes management platform to discover excursions. For example, given a time series of continuous glucose monitoring data, the diabetes management platform may detect all relative minima over windows of a certain timescale (e.g., 30 minutes, 60 minutes, 120 minutes, etc.). The diabetes management platform can pair successive minima into candidate excursion intervals, and then refine the candidate excursion intervals using one or more criteria. For example, the diabetes management platform may prevent an excursion interval from ending at a blood glucose level lower than where the excursion interval began. Moreover, the diabetes management platform may filter candidate excursion intervals having a height smaller than a certain amount (e.g., 10 mg/dL, 20 mg/dL, 30 mg/dL, etc.). These parameters (e.g., the certain timescale and the certain amount) may be personalized over time based on characteristics of the subject, such as recovery rate, average blood glucose value, etc.

In some embodiments, the diabetes management platform identifies excursions by applying patterns to detect matching parameter(s). The diabetes management platform may be communicatively coupled to a library of patterns corresponding to different glycemic events. For example, the library may include patterns that allow the diabetes management to readily identify instances of hypoglycemia, pre-sleep meals, administrations of medication, etc.

Figure 5A:
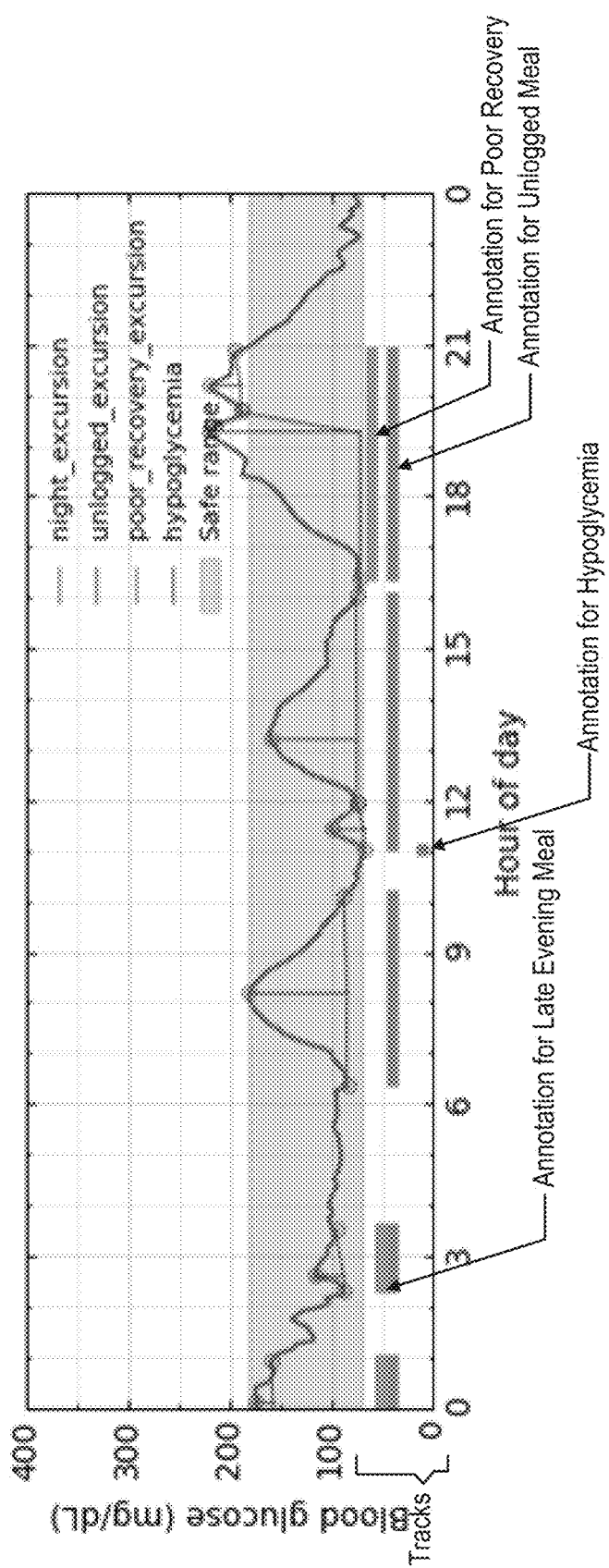
FIG. 5A depicts an example of a visualization that includes five annotations corresponding to unlogged meals, two annotations corresponding to late evening meals, one annotation corresponding to a hypoglycemic event, and one annotation corresponding to an instance of poor glycemic recovery.
Figure 5B:
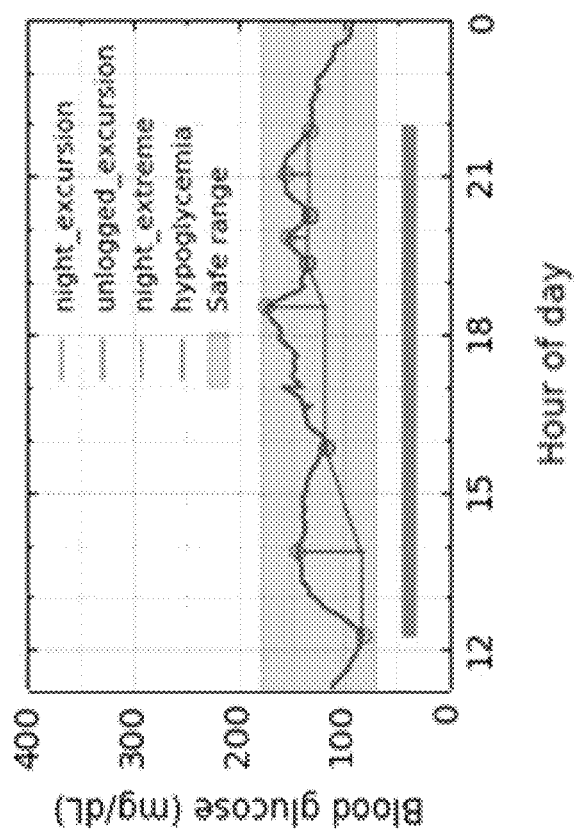
FIG. 5B depicts an example of a visualization that includes a single annotation corresponding to multiple unlogged meals.

FIGS. 5A-B illustrate how the diabetes management platform can automatically annotate a glucose trace to identify a variety of signal features indicative of different glycemic events. Examples of glycemic events include:

Meals that are unrelated to any subject-logged meals catalogued in a database. Often, a subject will manually log meals through a computer program associated with the diabetes management platform. The diabetes management platform may identify excursions that don't match a corresponding logged meal (e.g., through the comparison of time metadata derived from, or included with, the physiological data to records of logged meals).

Meals that are associated with an abnormally quick glycemic recovery (e.g., a glycemic recovery exceeding an upper rate) or an abnormally slow glycemic recovery (e.g., a glycemic recovery falling below a lower rate).

Meals that will cause the blood glucose level to exceed an upper threshold following consumption of the next meal. These meals will cause the blood glucose level to enter an unsafe glycemic range following the next meal.

Meals that occur within a certain proximity of a temporal event (e.g., a sleep cycle). For example, the diabetes management platform may detect meals that are consumed by subjects late in the evening to avoid having blood glucose level drop too low during the night. Because these events can be associated with medication problems, they provide a clear intervention point.

Meals that are substantially dissimilar from other meals in a nearby time interval (e.g., occurring in the same day or week), occurring at a similar time (e.g., occurring around the same time on consecutive days), etc. In some embodiments dissimilar meals are "bad" meals surrounded by "good" meals, while in other embodiments dissimilar meals are "good" meals surrounding by "bad" meals. A "bad" meal will generally cause the blood glucose level to exceed the upper threshold of the glycemic range recommended by the ADA. A "good" meal, meanwhile, will generally cause the blood glucose level to remain within the glycemic range recommended by the ADA.

Periodic patterns in the blood glucose value. For example, the diabetes management platform may detect that a subject struggles to stay within the recommended glycemic range during certain time periods (e.g., mornings, afternoons, evenings, or nights). Moreover, the diabetes management platform can infer information about the corresponding meals (i.e., breakfast, lunch, dinner, or sporadic snacks) based on the certain time periods.

Blood glucose values exceeding an upper threshold (e.g., 180 mg/dL, 200 mg/dL, 225 mg/dL, etc.).

Blood glucose values falling below a lower threshold (e.g., 60 mg/dL, 80 mg/dL, 100 mg/dL, etc.).

Figure 5C:
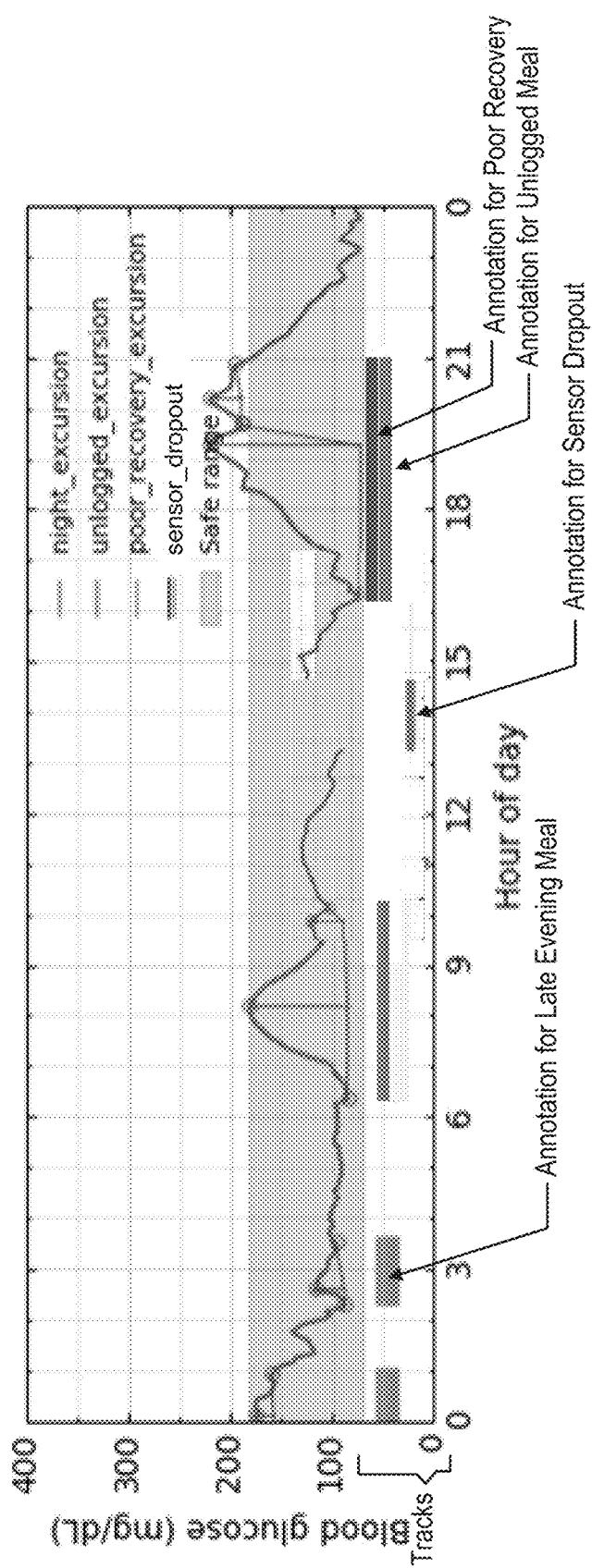
FIG. 5C depicts an example of a visualization that includes two annotations corresponding to unlogged meals, two annotations corresponding to late evening meals, one annotation corresponding to an instance of poor glycemic recovery, and one annotation corresponding to a sensor dropout.

Time intervals corresponding to glucose monitoring device-related issues. Examples of such issues include sensor dropout, faulty excursion data values, etc. The diabetes management platform may detect when sensor dropouts occur from gaps in physiological data, as shown in FIG. 5C. Sensor dropouts may be an indicator of poor placement/fit, replacement, etc.

Hypoglycemic events. Some glucose monitoring devices can generate hypoglycemia alerts based on a direct comparison of the blood glucose level to one or more thresholds. For example, some glucose monitoring devices generate alerts upon detecting blood glucose levels below a predefined threshold (e.g., 55 ml/dL) and a user-defined threshold (e.g., 70 mg/dL). However, the diabetes management platform may also be able to detect trends/instances of near hypoglycemia without necessarily triggering an alert. For example, the diabetes management platform may detect that a subject consistently has a low blood glucose level (e.g., 75 mg/dL) in the early morning hours (e.g., around 3:00 AM). Although the diabetes management platform may not generate an alert specifying a hypoglycemic event occurred, the diabetes management platform may notify a health coach of such behavior.

FIG. 5A depicts an example of a visualization that includes five annotations corresponding to unlogged meals, two annotations corresponding to late evening meals, one annotation corresponding to a hypoglycemic event, and one annotation corresponding to an instance of poor glycemic recovery. By making the annotations, the diabetes management platform can readily convey to a viewer of the visualization that a hypoglycemic event occurred at 11 AM and a very large excursion occurred at 5 PM that the subject didn't recover from until almost 11 PM.

Each annotation is associated with a corresponding time interval, whose duration is defined by the at least one pair of adjacent minima used to define the excursion. In some instances, a glycemic event may be defined by multiple excursions. Here, for example, a single annotation is used to represent the unlogged meals that occurred at 11 AM and 12 PM. Annotations may also partially or entirely overlap one another. Here, for example, the annotation corresponding to the instance of poor glycemic recovery covers the same time interval as one of the annotations corresponding an unlogged meal.

FIG. 5B depicts an example of a visualization that includes a single annotation corresponding to multiple unlogged meals. Here, the annotation indicates that the subject did not have sufficient time to recover following a large lunch at 12:30 PM, and thus was already experiencing an elevated blood glucose level prior to consuming dinner at 6:30 PM.

FIG. 5C, meanwhile, depicts an example of a visualization that includes two annotations corresponding to unlogged meals, two annotations corresponding to late evening meals, one annotation corresponding to an instance of poor glycemic recovery, and one annotation corresponding to a sensor dropout. Generally, sensor dropouts correspond to time intervals in which no physiological data has been acquired by the diabetes management platform. For example, physiological data may not be generated when the glucose monitoring device is replaced (e.g., on a weekly basis), the glucose monitoring device is dislodged (e.g., comes loose from the skin due to poor placement, loose tape, etc.), etc. As another example, physiological data may not be available if the communication channel between the glucose monitoring device and the computing device on which the diabetes management platform resides is disrupted. In such scenarios, the missing physiological data may not backfill if the glucose monitoring device is configured to stream physiological data to the computing device in real time.

As shown in FIGS. 5A-C, the visualizations may also depict the glycemic range recommended by the ADA. Here, the recommended glycemic range of 80 mg/dL to 180 mg/dL is highlighted gray. However, the upper threshold (i.e., 180 mg/dL) and the lower threshold (i.e., 80 mg/dL) could also be depicted using horizontal lines (e.g., solid, dashed, or dotted lines).

Additionally or alternatively, other glycemic ranges may be depicted in a visualization. For example, a subject whose blood glucose level is being monitored may be associated with a healthcare regimen that is intended to guide the subject toward a healthier glycemic range. In such embodiments, the glycemic range depicted in the visualization may change over time. Thus, the glycemic range may be 120-220 mg/dL during a first time interval, 100-200 mg/dL during a second time interval, etc. Gradual shifts in the glycemic range can facilitate improvement in the glycemic health state of the subject in a manner more susceptible to behavior change (e.g., because the subject can readily examine their blood glucose level with respect to the changing glycemic range).

Annotations of different types may be arranged along separate tracks positioned beneath the glucose trace. The separate tracks enable the diabetes management platform to depict multiple annotations that are easily distinguishable from one another, yet still temporally aligned. Thus, the separate tracks enable the diabetes management platform to easily classify a time interval as being indicative of multiple glycemic events (and thus multiple annotations). Here, for example, the time interval from 4-9 PM is associated with an annotation corresponding to an instance of poor glycemic recovery and an annotation corresponding to an unlogged meal. Annotations of different types may also be visually distinguishable from one another. For example, in some embodiments each type of annotation is associated with a different color, while in other embodiments each type of annotation is associated with a different line type (e.g., solid, dashed, dotted, etc.).

In some embodiments, annotations are also used to identify physiological data values that require further examination/analysis. For example, if a subject sleeps on a glucose monitoring device, then the data values generated by the glucose monitoring device may be artificially low due to poor readings. Because the diabetes management platform can readily determine that these low data values are not indicative of the true blood glucose level (e.g., by comparing to previous nights or monitoring a trend in the blood glucose level throughout the day), the diabetes management platform can identify the corresponding time interval as being a candidate for further analysis.

FIG. 6 depicts a flow diagram of a process 600 for making annotations to physiological data specifying the blood glucose level of a subject whose glycemic health state is being monitored. These annotations can be used to classify excursions detected in the physiological data to facilitate the identification of a therapeutic behavior change to be performed by the subject to improve the glycemic health state.

Initially, a diabetes management platform acquires physiological data generated by a glucose monitoring device (step 601). The physiological data can include a series of static measurements of the blood glucose level of the subject. Thus, the physiological data may include discrete, digitally represented values in a temporal order that are indicative of time-varying glucose concentration as sampled on a periodic or ad hoc basis.

The diabetes management platform can then post a visualization of the physiological data as a glucose trace over time to an interface for review by an individual (step 602). In some embodiments the individual is a person with diabetes, while in other embodiments the individual is interested in examining physiological data associated with some other person. Thus, the individual may be a health coach such as a medical professional (e.g., a physician or nurse), a diabetic health counselor, a family member, etc.

FIGS. 5A-C depict several examples of glucose traces constructed from measurements generated by a continuous glucose monitor. However, glucose traces could also be based on measurements generated by a blood glucose monitor, imputed measurements, or any combination thereof.

The diabetes management platform may also examine the physiological data to detect an excursion in the blood glucose level of the subject (step 603). More specifically, the diabetes management platform can detect a signal feature defined by one or more data values. Examples of signal features include the minimum blood glucose value, the maximum blood glucose value (also referred to as the "peak blood glucose value"), the total area beneath the peak blood glucose value (i.e., an integral of a glucose trace over the duration of the peak blood glucose value), a recovery rate following the peak blood glucose value, a time characteristic of the minimum or peak blood glucose values, etc. Thus, while some excursions may be defined by blood glucose level variations exceeding a specified amount, other excursions may be based on the magnitude of a single data value (e.g., in the case of the minimum and peak blood glucose values).

Several different techniques can be employed for detecting excursions in the blood glucose level of the subject. In some embodiments, the diabetes management platform detects an excursion that exceeds a specific threshold, selects a time interval that includes the excursion, and classifies, in response to selecting the time interval, the data value(s) defining the excursion as being indicative of a glycemic event. In other embodiments, the diabetes management platform segments the physiological data into multiple time intervals, classifies each time interval of the multiple time intervals based on the presence of any glycemic events, merges consecutive time intervals having the same classification, and identifies, from both the merged and unmerged time intervals, a time interval corresponding to a certain glycemic event. Accordingly, the multiple time intervals examined by the diabetes management time intervals may include both merged and unmerged time intervals (e.g., consecutive time intervals having the same classification are a subset of the multiple time intervals). Thus, the time interval under consideration may be a single time interval or a combined time interval formed from more than one of the multiple time intervals.

The diabetes management platform can then classify the excursion as being indicative of a glycemic event (step 604). The term "glycemic event" broadly refers to any event that affects the blood glucose level. Examples of such events include the performance of an exercise activity, consumption of a foodstuff, administration of a medication, etc. Thus, the diabetes management platform may determine that a upward variation in the blood glucose level exceeding a certain amount likely corresponds to consumption of a foodstuff. Similarly, the diabetes management platform may determine that a downward variation in the blood glucose level exceeding a certain amount likely correspond to administration of a medication. In some embodiments, the diabetes management platform can detect characteristic(s) of the glycemic event based on feature(s) of the excursion. For example, if the upward variation in the blood glucose level exceeds a certain threshold, then the diabetes management platform may determine that the subject likely consumed a large meal or a meal high in carbohydrates. Examples of such excursion features include the total variation in the blood glucose level, duration of the excursion, maximum/minimum values, etc.

The diabetes management platform can also identify an annotation corresponding to the glycemic event (step 605). For example, responsive to classifying the excursion as being indicative of a glycemic event, the diabetes management platform may designate an annotation for a target time period based on the glycemic event. In some embodiments, the target time period is the same as the time interval over which the signal feature is present. In other embodiments, the target time period is a subset of the time interval over which the signal feature is present. Said another way, the time interval may be a superset of the target time period. For example, the time interval may include an onset period preceding the annotated glycemic event and/or a tail period following the annotated glycemic event, The diabetes management platform can then cause display of the annotation on the interface for review by the individual (step 606). As shown in FIGS. 5A-C, the diabetes management platform can represent the annotation as a horizontal line arranged beneath a corresponding window of physiological data represented as a glucose trace. The glucose trace and the annotation can be aligned with respect to a common time axis, thereby visually alerting the individual of potential changes in the glycemic health state of the subject.

The diabetes management platform will often characterize continuous windows of physiological data with different annotation(s). As shown in FIGS. 5A and 5C, a visualization can include multiple annotations. Moreover, because an excursion may be indicative of multiple types of glycemic events, the diabetes management platform may overlay multiple annotations on top of one another (e.g., by arranging each annotation along a separate track beneath the glucose trace). Visual presentation of these annotations can facilitate the discovery of the glycemic health state of the subject, the recommendation of a therapeutic behavior change for improving the glycemic health state, the identification of comparable subjects and/or glycemic events, etc.

In some embodiments, the diabetes management platform further stores an indication of the annotation in a database to create a historical record of annotations associated with the subject (step 607). Because each annotation is associated with a glycemic event, the historical record of annotations can also represent a historical record of glycemic events experienced by the subject. More specifically, the diabetes management platform can configure a subject profile in the database to specify that the glycemic event occurred at a certain time. Thus, the subject profile can include an entry for each glycemic event, a time interval during which the glycemic event occurred, etc. In some embodiments the time interval is dynamically generated (e.g., by identifying a start time corresponding to initiation of the excursion and an end time corresponding to conclusion of the excursion), while in other embodiments the time interval is selected from a predetermined list (e.g., by determining whether the glycemic event occurred during the morning, afternoon, evening, or night).

When the annotations are stored in the database, the diabetes management platform can perform various operations. For example, the diabetes management platform may receive input indicative of a request to identify similar instance(s). Thus, a health coach may ask to see instances where the subject experienced hypoglycemia, a blood glucose level exceeding 100 mg/dL during the night, a sensor dropout, etc. Moreover, the diabetes management platform may perform browsing/filtering of the historical record of annotations. Thus, a health coach may ask to see instances where the subject concurrently experienced two different glycemic events. These features are particularly useful for health coaches who are responsible for reviewing large sets of physiological data (e.g., for hundreds of subjects or over hundreds of days).

FIG. 7 depicts a flow diagram of a process 700 for facilitating the acquisition of feedback from an individual for improving the glycemic health state of a subject whose blood glucose level is being monitored. As noted above, the individual may be the subject or some other person, such as a health coach responsible for monitoring the glycemic health state of the subject.

Initially, a computer program executing on a computing device will generate an interface accessible to an individual (step 701). The computer program can then post a visualization of physiological data as a glucose trace to the interface for review by the individual (step 702). The visualization can take several different forms. FIGS. 5A-C depict several examples of glucose traces generated over different time intervals.

The computer program can then compile a visualization component that identifies excursions in the physiological data that represent glycemic events. More specifically, the computer program can populate one or more tracks arranged alongside the glucose trace with one or more annotations (step 703). Generally, the track(s) are located beneath the glucose trace. However, the track(s) could be located above the glucose trace. Moreover, the computer program may overlay the track(s) on the glucose trace, in which case the annotations may appear when the individual hovers over the corresponding window of the glucose trace.

While separate tracks are useful when multiple annotations are associated with a single time interval, other visualization components can also be compiled. For example, the computer program may generate text-based annotations that label specific time intervals. As another example, the computer program may distinguish certain time intervals using vertical lines (e.g., solid, dashed, or dotted lines) or shaded segments to identify individual excursions.

In some embodiments, the computer program is configured to dynamically modify the visualization and/or the visualization component in real time (step 704). For example, upon acquiring new physiological data, the computer program can modify the glucose trace to indicate that new information is available regarding the time-varying blood glucose level. As another example, the computer program may automatically begin examining new physiological data to identify excursions in the physiological data. Thus, the computer program may identify glycemic events represented by excursions in the physiological data, as well as predict which glycemic event(s) are likely to occur in the future based on patterns in the physiological data. For example, the computer program may determine that if the blood glucose level falls below a lower threshold, then the subject is likely to overconsume at their next meal. In such a scenario, the computer program may proactively notify the subject that they should be mindful of how much food is being consumed and/or notify the health coach to provoke proactive coaching before an unhealthy glycemic health state is reached.

The computer program can estimate a glycemic health state of the subject based on the visualization and/or the visualization component (step 705). The glycemic health state may be based on the annotation and/or other characteristics of the excursion, such as duration, frequency, intensity, etc. For example, the computer program may apply a rule set that specifies the number of annotations within a time interval (e.g., a 24-hour period matching a circadian cycle) is inversely proportional to the glycemic health state. Generally, the more annotations within a time interval, the more likely the subject is in a "bad" glycemic health state.

The computer program can also estimate a glucose-related metric based on the physiological data series (step 706). Examples of glucose-related metrics include time-in-range, mean glucose, day-estimated A1c level, standard deviation of the blood glucose level, coefficient of variation of the blood glucose level, etc. The computer program may post the glucose-related metric to the interface for review by the individual, store the glucose-related metric in a database record associated with a subject profile, etc.

If the individual is a health coach responsible for monitoring the glycemic health of another person (also referred to as a "subject" or "patient"), then the computer program may receive input indicative of feedback provided through the interface (step 707). The feedback may include a recommendation of a therapeutic behavior change intended to improve the subject's glycemic health state. For example, the health coach may identify certain activities or foodstuffs that are associated with a decline in glycemic health, and thus should be avoided. As another example, the health coach may identify certain activities or foodstuffs that are associated with an improvement in glycemic health, and thus should be performed. In such embodiments, the computer program may cause display of a notification by another computer program executing on another computing device associated with the subject (step 708). For example, the computer program may communicate directly with the other computer program through a simple messaging technology. As another example, the computer program may transmit the notification to a diabetes management platform, which may be responsible for forwarding the notification to the other computer program.

Other steps may also be performed. For example, if the individual is the subject whose blood glucose level is being monitored, then the computer program may automatically display a recommendation for improving the glycemic health state. Thus, the recommendation may not be based on feedback provided by a health coach. Instead, the computer program could dynamically identify appropriate feedback based on the excursions, glycemic events, or annotations. As another example, the computer program may prioritize a pool of subjects for review by the health coach based on the number of annotations corresponding to each subject, the type of annotations corresponding to each subject, the level of subject involvement (e.g., based on the number of unlogged meals detected), etc. These criteria can be used to identify those subject(s) that are having the most difficulty maintaining a healthy glycemic state. Prioritization enables the health coach to provide feedback to those subjects who consistently struggle to maintain their glycemic health before those subjects who occasionally struggle to maintain their glycemic health.

Moreover, the computer program may enable the health coach to compile other visualization components based on the excursions, glycemic events, or annotations. These visualization components could include text, audio, video, or any combination thereof. Some visualization components only include text specifying a recommendation for improving glycemic health, while other visualization components include audio and/or video for incentivizing future performance of certain activities (e.g., logging meals may be incentivized by showing digital balloons, confetti, congratulatory messages, etc.).

Unless contrary to physical possibility, it is envisioned that the steps described above may be performed in various sequences and combinations. For example, the diabetes management platform may simultaneously notify a subject whose blood glucose level is being monitored and a health coach responsible for monitoring the glycemic health of the subject. As another example, the diabetes management platform may periodically execute these processes such that visualizations and annotations are generated on a periodic basis (e.g., daily, weekly, or monthly).

Other steps may also be included in some embodiments. For example, the diabetes management platform may perform an analytic process on physiological data to detect whether there are any time intervals in which the blood glucose measurements are rarely taken. Such action may be performed selectively, For instance, the diabetes management platform may only perform the analytic process responsive to discovering the physiological data was generated by a blood glucose monitor that generates blood glucose measurements on an ad hoc basis. An annotation may be generated to identify these time intervals with sporadic coverage. Other examples of analytic processes include prioritizing recommendations provided for improving the glycemic health state of the subject, examining glucose-related metrics critical in guiding diabetes management in a personalized manner, posting certain glucose-related metrics and/or visualizations to an interface for review by the subject or a health coach, etc.

Processing System

Figure 8:
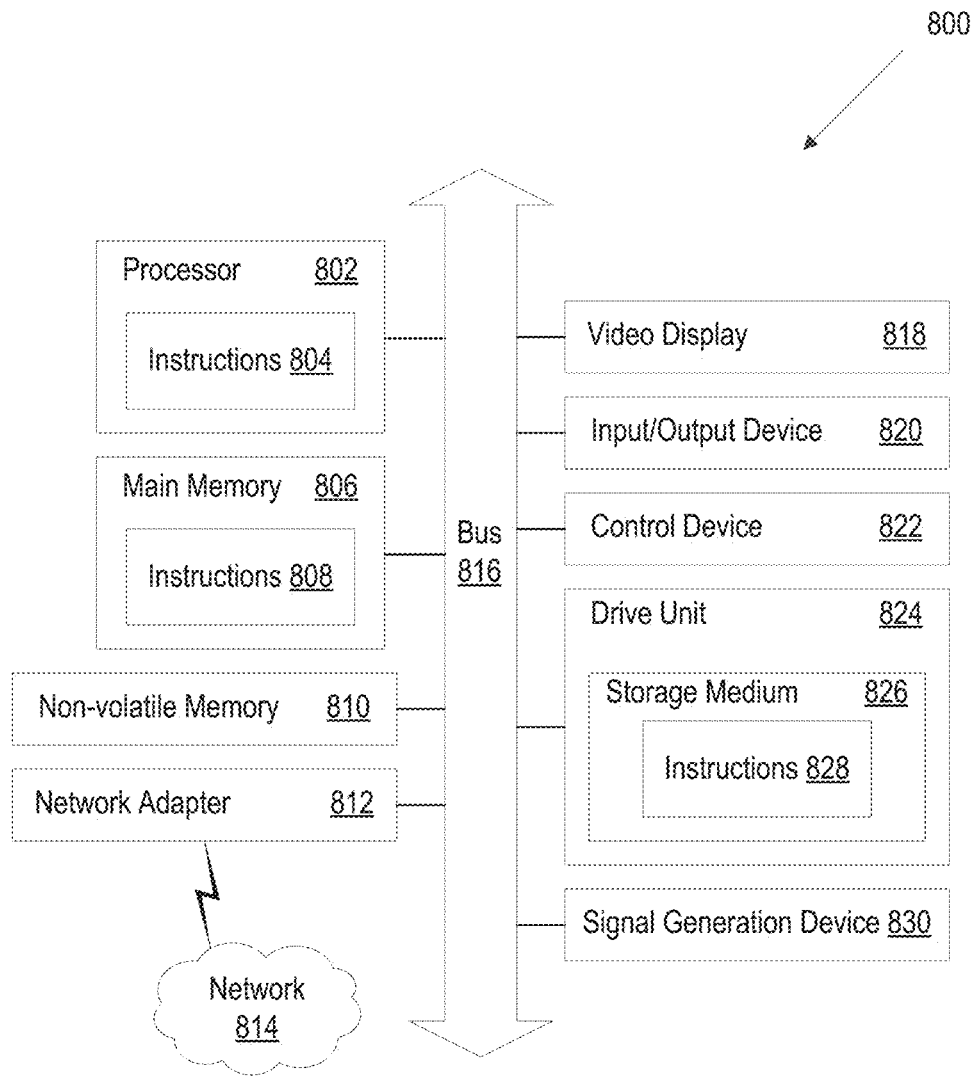
FIG. 8 is a block diagram illustrating an example of a processing system in which at least some operations described herein can be implemented.

FIG. 8 is a block diagram illustrating an example of a processing system 800 in which at least some operations described herein can be implemented. For example, some components of the processing system 800 may be hosted on a computing device that includes a diabetes management platform (e.g., diabetes management platform 102 of FIG. 1).

The processing system 800 may include one or more central processing units ("processors") 802, main memory 806, non-volatile memory 810, network adapter 812 (e.g., network interface), video display 818, input/output devices 820, control device 822 (e.g., keyboard and pointing devices), drive unit 824 including a storage medium 826, and signal generation device 830 that are communicatively connected to a bus 816. The bus 816 is illustrated as an abstraction that represents one or more physical buses and/or point-to-point connections that are connected by appropriate bridges, adapters, or controllers. The bus 816, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 800 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 800.

While the main memory 806, non-volatile memory 810, and storage medium 826 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 828. The term "machine-readable medium" and "storage medium" shall also be taken to include any medium that is capable of storing, encoding, or carrying a set of instructions for execution by the processing system 800.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 804, 808, 828) set at various times in various memory and storage devices in a computing device. When read and executed by the one or more processors 802, the instruction(s) cause the processing system 800 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 810, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 812 enables the processing system 800 to mediate data in a network 814 with an entity that is external to the processing system 800 through any communication protocol supported by the processing system 800 and the external entity. The network adapter 812 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 812 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:
   receiving, by a processor, physiological data generated by a glucose monitoring device that monitors a blood glucose level of a subject;
   examining, by the processor, the physiological data to discover a series of values that match a pattern in accordance with a pattern-defining parameter,
      wherein the series of values includes a pair of semi-global minima values with a peak value therebetween;
   designating, by the processor, an annotation indicative of a glycemic event to a target time period that corresponds to the series of values; and
   posting, by the processor, the annotation on an interface that includes a visualization of the physiological data as a glucose trace.

2. The method of claim 1,
   wherein the physiological data includes discrete values in a temporal order that are indicative of the blood glucose level at corresponding points in time, and
   wherein the physiological data includes multiple sets of values representative of measurements of the blood glucose level at regular intervals.

3. The method of claim 1, further comprising:
storing, by the processor, an indication of the annotation in a database to create a historical record of glycemic events experienced by the subject.

4. The method of claim 1, wherein the annotation is temporally aligned with the glucose trace with respect to a common time axis.

5. The method of claim 1, wherein the series of values is associated with an interval of time, and wherein the method further comprises:
identifying, by the processor, a past interval of time associated with another series of values that is substantially similar to the series of values of the interval of time; and
causing, by the processor, display of a visualization component that specifies the past interval of time on the interface.

6. The method of claim 5, wherein the interval of time is a superset of the target time period.

7. The method of claim 1, wherein said examining comprises:
applying a classification model that is trained to identify the series of values in the physiological data responsive to determining that a matching window of physiological data corresponds to a meal.

8. The method of claim 1, wherein said examining comprises:
detecting that an excursion defined by the series of values exceeds a threshold,
selecting an interval of time that includes the excursion, and
classifying the series of values as being indicative of the glycemic event based on the interval of time.

9. The method of claim 1, further comprising:
configuring, by the processor, a profile associated with the subject in the database to specify that the glycemic event occurred during a certain interval of time.

10. A non-transitory computer-readable medium with instructions stored thereon that, when executed by a processor, cause the processor to perform operations comprising:
acquiring physiological data generated by a glucose monitoring device that monitors a blood glucose level of a subject;
detecting a signal feature by examining the physiological data to discover a series of values that satisfy a pattern-defining parameter;
identifying an interval of time that corresponds to the series of values;
classifying the series of values as being indicative of a glycemic event based on the signal feature and the interval of time; and
configuring a profile associated with the subject in a database to specify that the glycemic event occurred during the interval of time.

11. The non-transitory computer-readable medium of claim 10, wherein the operations further comprise:
posting a visualization of the physiological data as a glucose trace to an interface generated by the computer program executing on the computing device; and
causing display of an annotation indicative of the glycemic event on the interface such that the annotation is temporally aligned with the glucose trace with respect to a common time axis.

12. The non-transitory computer-readable medium of claim 10, wherein the signal feature is an area of an excursion defined by the series of values.

13. The non-transitory computer-readable medium of claim 10, wherein the signal feature is a recovery rate following a minimum value or a maximum value within a configurable interval.

14. The non-transitory computer-readable medium of claim 10, wherein the signal feature is a timing characteristic of a minimum value or a maximum value within a configurable interval.

15. The non-transitory computer-readable medium of claim 11, wherein the interface includes annotations designated for multiple subjects, and wherein said causing is performed for the purpose of prioritizing the multiple subjects for examination.

16. The non-transitory computer-readable medium of claim 11, wherein said causing is performed for the purpose of facilitating the identification of a therapeutic behavior change to be performed by the subject to improve a glycemic health state.

17. The non-transitory computer-readable medium of claim 10, wherein the glycemic event is—
a meal that is unrelated to any subject-logged meals catalogued in the database,
a meal that is associated with a glycemic recovery exceeding a threshold,
a meal that will cause the blood glucose level to exceed an upper threshold following consumption of a next meal,
a meal that occurred within a certain proximity of a sleep cycle,
a maximum blood glucose value exceeding the upper threshold,
a minimum blood glucose value falling below a lower threshold,
a time window for which physiological data is not available,
a hypoglycemic event, or
any combination thereof.

18. A method comprising:
receiving, by a processor, physiological data that includes discrete values indicative of a blood glucose level of a subject at corresponding points in time;
examining, by the processor, the physiological data to discover an excursion defined by a series of values that satisfy a pattern-defining parameter;
classifying, by the processor, the excursion as being indicative of a glycemic event based on a characteristic of the series of values;
designating, by the processor, an annotation indicative of the glycemic event to the excursion;
identifying, by the processor based on the glycemic event, a recommendation regarding a therapeutic behavior change intended to improve a glycemic health state of the subject; and
posting, by the processor, the annotation and the recommendation to an interface generated by a computer program executing on a computing device.

19. The method of claim 18, wherein the series of values includes a pair of semi-global minima values with a peak value therebetween.

20. The method of claim 18, wherein the characteristic is a peak maximum value, a peak minimum value, a total magnitude of the excursion, or a total duration over which the excursion occurs.

* * * * *